United States Patent [19]
Jordaan et al.

[11] Patent Number: 5,360,898
[45] Date of Patent: Nov. 1, 1994

[54] PRODUCTION OF AN ORGANIC SALT OF A RARE EARTH METAL

[75] Inventors: Amor Jordaan; Petrus J. Stander, both of Sasolburg, South Africa

[73] Assignee: Sentrachem Limited, Sandown, South Africa

[21] Appl. No.: 19,619

[22] Filed: Feb. 19, 1993

[30] Foreign Application Priority Data

Feb. 28, 1992 [ZA] South Africa ................. 92/1518

[51] Int. Cl.$^5$ ............... C07C 51/41; C07C 61/00; C07C 53/128
[52] U.S. Cl. ................................................ 534/16
[58] Field of Search ....................................... 534/16

[56] References Cited
U.S. PATENT DOCUMENTS 5,017,539 5/1991 Jenkins et al. .
5,154,764 10/1992 Cells et al. .

Primary Examiner—Gary Geist
Attorney, Agent, or Firm—Fish & Richardson

[57] ABSTRACT

A method for making a rare earth metal salt of an organic acid, for example neodymium naphthenate, is provided. The method includes the steps of producing a three-phase system which comprises an aqueous phase in which is dissolved a salt of a rare earth metal or an alkali metal or alkaline earth metal salt, a solid water-insoluble rare earth compound suspended in the aqueous phase, and an organic phase containing the organic acid. The organic acid is allowed to distribute between the organic and aqueous phases, react with the dissolved inorganic salt and release an inorganic acid. This leads to some of the water-insoluble rare earth compound becoming dissolved in the aqueous phase and reacting with the organic acid to form a rare earth metal salt of the organic acid. The rare earth metal salt of the organic acid is allowed to transfer to the organic phase from whence it is recovered.

13 Claims, No Drawings

PRODUCTION OF AN ORGANIC SALT OF A RARE EARTH METAL

BACKGROUND OF THE INVENTION

This invention relates to the production of a rare earth metal (lanthanide) salt of an organic acid.

Rare earth metal naphthenates, particularly neodymium napthenate, have use as part of the catalyst in the production of 1,4-butadiene rubbers. A number of methods are known for producing neodymium naphthenate.

One of these methods is the precipitation method. In this method, a water-soluble neodymium salt such as neodymium chloride reacts with a water-soluble naphthenate salt such as sodium naphthnate. The reaction takes place in an aqueous medium and the neodymium naphthenate is extracted into an organic solvent such as hexane. This method is cumbersome as the neodymium chloride is usually first prepared from neodymium oxide and the sodium naphtherate from sodium hydroxide and naphthenic acid.

Another method of producing neodymium naphthenate is by the direct reaction of neodymium oxide and naphthenic acid. The problem with this method is that high temperatures are required and that a viscous product is obtained. Also, it is difficult to avoid employing an excess of naphthenic acid.

In a further method solvent extraction is used whereby an aqueous solution of a lanthanide salt to which organic acids such as naphthenic acids or sulphonic acid have been added are extracted with organic solvents. As equilibria are quickly set up between the different components, this method has the disadvantage of low efficiency and low recovery of product.

SUMMARY OF THE INVENTION

According to the present invention, a method of making a rare earth metal salt of an organic acid includes the steps of producing a three-phase system comprising an aqueous phase in which is dissolved an inorganic salt which is a salt of a rare earth metal, or of an alkali metal, or of an alkali earth metal, a solid water-insoluble rare earth compound suspended in the aqueous phase, and an organic phase containing an organic acid, allowing the organic acid to distribute between the organic and aqueous phases, react with the dissolved inorganic salt and release an inorganic acid, allowing the inorganic acid to react with at least some of the water-insoluble rare earth compound which becomes dissolved in the aqueous phase and reacts with the organic acid to form a rare earth metal salt of the organic acid, and allowing the rare earth metal salt of the organic acid thus formed to transfer to the organic phase.

DESCRIPTION OF EMBODIMENTS

The insoluble rare earth compound is caused to dissolve in the aqueous phase by reaction with a transient inorganic acid intermediate which is released through reaction of a water-soluble salt with an organic acid such as naphthenic acid. The water-soluble salt of the rare earth metal is never fully depleted as it is continuously being regenerated so that in a sense it acts as a phase transfer agent or facilitator for transfer of the rare earth metal as a salt to the organic phase via further dissolution of the insoluble rare earth compound through reaction with inorganic acid released in the aqueous phase. The water-soluble salt may be added to the aqueous phase, or it may be formed in situ.

The water-soluble or dissolved inorganic salt which is used to aid solubilisation and extraction of the insoluble rare earth compound, i.e. the phase transfer facilitator, may be selected from a range of salts. For example, the salt may be a rare earth metal salt such as a chloride. A sulphate, a nitrate or a phosphate. The water-soluble salt may also be an alkali or alkaline earth metal chloride, nitrate, sulphate or phosphate. The inorganic acids released by such salts in the practice of the method of the invention are hydrochloric acid, nitric acid, sulphuric acid and phosphoric acid, respectively.

The water-soluble inorganic salt may be added to the aqueous phase in the form of the salt itself. Alternatively, it may be formed in situ. This may be achieved, for example, by the addition of a water-insoluble salt or oxide and an aliquot of a suitable acid which, by chemical reaction, solubilises at least some of a water-insoluble salt or oxide.

The three-phase system is preferably an intimate mixture of the three phases maintained, for example, by agitation. To assist in transfer of the organic salt from the aqueous phase to the organic phase, the phases are preferably vigorously mixed, for example, by stirring or shaking.

The water-insoluble rare earth compound which is suspended in the aqueous phase may be added incrementally or at one time.

The process may be carried out on a batch or continuous basis. In particular, the organic phase rich in the rare earth metal salt of an organic acid, may be removed periodically or continuously for further processing.

The rare earth metals are a group of 15 chemically related elements in Group IIIB of the Periodic Table and are also known as the lanthanide series. Any rare earth metal may be used in the practice of the invention. Neodymium is particularly preferred because neodymium naphthenate, for example, is a useful catalyst component for the production of 1,4-butadiene rubbers.

The organic acid is preferably a naphthenic, versatic or other alkanoic acid capable of forming rare earth alkanoates which are soluble in organic solvents. Naphthenic acids are a group of saturated fatty acids recovered from crude petroleum and petroleum distillates, while versatic acids are synthetic, saturated, highly branched carboxylic acid mixtures.

The water-insoluble rare earth compound can be an oxide, a hydroxide, a carbonate, or a bicarbonate which is dissolved by aqueous acid.

The organic solvent can be any aromatic solvent such as toluene or benzene, an alkane solvent such as pentane or hexane, a cloalkane solvent such as cyclohexane, an alkene solvent or a mixture containing any one of these solvents.

The concentration of the water-soluble inorganic salt in the aqueous phase does not affect the reaction rate to any large extent. An example of a range tested is 0,0075 mole $Nd^{3+}$/100g of aqueous phase to 0.15 mole $Nd^{3+}$/100g of aqueous phase.

Similarly, the ratio of moles of water-soluble inorganic salt to moles of water-insoluble rare earth compound may vary within wide limits. For example, ratios ranging between 1 to 0.5 moles and 1 to 15 moles of rare earth ion to rare earth oxide result in high reaction rates.

The organic solvent which after phase separation contains the required rare earth organic acid salt can be dried by azeotropically removing water through distilling off a portion of the organic solvent. Dry solvent can be added during the azeotropic distillation to ensure that solvent levels and water impurities are acceptable for further application of the solution.

The temperature at which the three-phase system is maintained is not critical. For an effective reaction time, it is preferred that the temperature is maintained at a temperature exceeding 50° C.

The invention has particular application to the production of neodymium versatate and neodymium naphthenate. For the production of these salts, the following preferred conditions are mentioned.

1) The synthesis of neodymium product which is transferred to the organic solvent phase proceeds at high rates at both 50° C. and 70° C. Lower temperatures can also be employed, but reactions are faster at higher temperatures. To obtain very fast reactions, temperatures above 100° C. and which necessitate the use of pressure vessels may be employed.

2) Naphthenic or versatic acid is dissolved in organic solvent to lower the viscosity of the formed neodymium salt solution. Concentrations between 70% (w/w) and 40% (w/w) acid in hexane solvent are suitable, although either higher or lower concentrations can be gainfully employed. Other organic solvents such as toluene, alkanes and cycloalkanes and the like are also suitable.

The following examples illustrate the method of the invention.

EXAMPLE 1

Naphenic acid (acid number 236; 0,36 mole; 85g) dissolved in hexane (150ml) is added to $Nd(NO_3)_3$ (aq) (0,015 mole; [Nd]=$7.5 \times 10^{-2}$ mole/ 100g of aqueous phase) in a 500ml round bottom flask equipped with a heating mantle, a stirrer and a reflux condenser. $Nd_2O_3$ (0.06 mole; 20.2g) is incrementally added in ten portions of about 2g each. About 7 minutes reaction time is allowed between the addition of each portion. When the addition is completed, the reaction mixture is stirred vigorously for another 60 minutes. The reaction temperature is maintained at 62° C.

The organic layer is decanted and washed with water (200ml). Hexane (400ml) is added before drying the product by azeotroping hexane (400ml) from the solution.

The final Nd-conversion is 95%.

EXAMPLE 2

Versatic acid (MW 175; 31,5g; 0,18 mole) dissolved in hexane (50ml) is added to $NdCl_3$(aq) (0,015 mole; [Nd]=0.137 mol/100g solution; pH=5.7) in a 300 ml round bottomed flask equipped with a heating mantle, a stirrer and a reflux condenser. $Nd_2O_3$ (0.03 mole; 10.08g) is wetted with water (4g) and added to the mixture while stirring. The reaction is allowed to proceed for 15 minutes at 50° C.

The organic layer is decanted and washed with deionised water. Hexane (200ml) is added before drying the product by removing the hexane/water azeotrope (200ml).

The final Nd conversion is 92%.

EXAMPLE 3

To an aqueous solution of $Nd(NO_3)_3$ (0,03 mole; [Nd]=$6.5 \times 10^{-4}$ mol/g; solution pH=2) naphthenic acid (85g; 0,36 mole) dissolved in hexane (100ml) is added. The same equipment is used as for Example 1. $Nd_2O_3$ (20.2g; 0.06 mole) is added to the stirred mixture. The reaction temperature is maintained at 60° C. for 10 minutes.

After decantation of the organic layer the above procedure is repeated by using the same recovered aqueous solution of $Nd(NO_3)_3$ for two further syntheses. Neodymium naphthenate yields for the three successive preparations are 90%, 86% and 88%, respectively.

We claim:

1. A method of making a rare earth metal salt of an organic acid includes the steps of producing a three-phase system comprising an aqueous phase in which is dissolved an inorganic salt which is a salt of a rare earth metal, or of an alkali metal, or of an alkali earth metal, a solid water-insoluble rare earth compound suspended in the aqueous phase, and an organic phase containing an organic acid, allowing the organic acid to distribute between the organic and aqueous phases, react with the dissolved inorganic salt and release an inorganic acid, allowing the inorganic acid to react with at least some of the water-insoluble rare earth compound which becomes dissolved in the aqueous phase and reacts with the organic acid to form a rare earth metal salt of the organic acid, and allowing the rare earth metal salt of the organic acid thus formed to transfer to the organic phase.

2. A method according to claim 1 wherein the three-phase system is an intimate mixture of the three phases.

3. A method according to claim 2 wherein the intimate mixture is maintained by agitation.

4. A method according to claim 1 wherein the organic phase rich in the rare earth metal salt is removed periodically or continuously for further processing.

5. A method according to claim 1 wherein the organic acid is an alkanoic acid.

6. A method according to claim 1 wherein the organic acid is naphthenic or versatic acid.

7. A method according to claim 1 wherein the rare earth metal is neodymium.

8. A method according to claim 1 wherein the water-soluble inorganic salt is a rare earth metal chloride, sulphate, nitrate or phosphate.

9. A method according to claim 1 wherein the water-soluble inorganic salt is an alkali or alkaline earth metal chloride, nitrate, sulphate or phosphate.

10. A method according to claim 1 wherein the water-insoluble rare earth compound is selected from oxides, hydroxides, carbonates and bicarbonates.

11. A method according to claim 1 wherein the organic solvent organic phase comprises an selected from aromatic, alkane, cycloalkane and alkene solvents and mixtures thereof.

12. A method according to claim 1 wherein the organic phase comprises an organic solvent is selected from toluene, benzene, pentane, hexane, cyclohexane and mixtures thereof.

13. A method according to claim 1 wherein the temperature of the three-phase system is maintained above 50° C.

* * * * *

UNITED STATES PATENT AND TRADEMARK OFFICE
CERTIFICATE OF CORRECTION

PATENT NO. : 5,360,898

DATED : November 1, 1994

INVENTOR(S) : Amor Jordaan and Petrus J. Stander

It is certified that error appears in the above-identified patent and that said Letters Patent is hereby corrected as shown below:

Col. 1, line 21; "naphtherate" should be --naphthenate--.

Col. 2, line 7; "chloride." should be --chloride,--.

Col. 2, line 8; "A" should be --a--.

Col. 2, Line 53; "cloalkane" should be --cycloalkane--.

Col. 4, lines 56-57; delete "organic solvent organic phase comprises an" and substitute --organic phase comprises an organic solvent--.

Col. 4, line 61; delete the word "is".

Signed and Sealed this

Second Day of May, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,360,898

DATED : November 1, 1994

INVENTOR(S) : Amor Jordaan and Petrus J. Stander

It is certified that error appears in the above-identified patent and that said Letters Patent is hereby corrected as shown below:

Col. 3, line 35; "Naphenic should be --Naphthenic--.

Signed and Sealed this

Thirteenth Day of June, 1995

Attest:

BRUCE LEHMAN

Attesting Officer            Commissioner of Patents and Trademarks